United States Patent
Frey et al.

(10) Patent No.: US 8,480,877 B2
(45) Date of Patent: Jul. 9, 2013

(54) SENSOR ARRANGEMENT COMPRISING AN ELECTRODE FOR DETECTING DIFFUSED LOADED PARTICLES

(75) Inventors: Alexander Frey, München (DE); Franz Hofmann, München (DE)

(73) Assignee: Siemens Aktiengesellschaft, Munich (DE)

(*) Notice: Subject to any disclaimer, the term of this patent is extended or adjusted under 35 U.S.C. 154(b) by 1296 days.

(21) Appl. No.: 11/597,296

(22) PCT Filed: May 24, 2005

(86) PCT No.: PCT/DE2005/000945
§ 371 (c)(1),
(2), (4) Date: Aug. 10, 2009

(87) PCT Pub. No.: WO2005/116244
PCT Pub. Date: Dec. 8, 2005

(65) Prior Publication Data
US 2009/0308741 A1 Dec. 17, 2009

(30) Foreign Application Priority Data
May 25, 2004 (DE) .......................... 10 2004 025 580

(51) Int. Cl.
*G01N 27/327* (2006.01)
*G01N 27/416* (2006.01)

(52) U.S. Cl.
USPC .................. 205/792; 204/403.01; 204/412

(58) Field of Classification Search
USPC 204/403.01, 403.03, 409, 412, 416; 205/779, 205/780, 792, 793.5
See application file for complete search history.

(56) References Cited

U.S. PATENT DOCUMENTS 7,208,077 B1 * 4/2007 Albers et al. .................. 205/782
7,413,859 B2 * 8/2008 Paulus et al. .................. 435/6.1
(Continued)

FOREIGN PATENT DOCUMENTS

DE 301 930 A9 7/1994
DE 196 10 115 A1 9/1997
(Continued)

OTHER PUBLICATIONS

F.Hofmann et al.: "Passive DNA Sensor with Gold Electrodes Fabricated in a CMOS Backend Process", Proceedings ESSDERC 2002, Digit of Tech.Papers, pp. 487-490.
(Continued)

*Primary Examiner* — Keith Hendricks
*Assistant Examiner* — Susan D Leong
(74) *Attorney, Agent, or Firm* — Harness, Dickey & Pierce, P.L.C.

(57) ABSTRACT

A sensor arrangement for detecting particles potentially contained in an analyte is disclosed. The arrangement includes a substrate; at least one sensor electrode which is arranged on and/or in the substrate and on which scavenger molecules, which hybridize with particles that are potentially contained in an analyte and are to be detected, are immobilized, electrically charged particles generated by hybridization being detectable on the at least one sensor electrode; and at least one diffusion detection electrode which is arranged in a surrounding region of the at least one sensor electrode and is embodied in such a way that it detects electrically charged particles that are generated by hybridization and can be diffused away by the at least one sensor electrode.

24 Claims, 6 Drawing Sheets

U.S. PATENT DOCUMENTS

| | | |
|---|---|---|
| 2002/0028441 A1 | 3/2002 | Hintsche et al. |
| 2003/0155237 A1 | 8/2003 | Surridge et al. |
| 2004/0014054 A1 | 1/2004 | Frey et al. |
| 2004/0063152 A1 | 4/2004 | Gumbrecht et al. |

FOREIGN PATENT DOCUMENTS

| | | |
|---|---|---|
| DE | 100 15 816 A1 | 10/2001 |
| DE | 100 58 397 A1 | 6/2002 |
| DE | 101 09 777 A1 | 9/2002 |
| DE | 101 26 341 A1 | 12/2002 |
| DE | 101 45 700 A1 | 4/2003 |
| DE | 102 14 719 A1 | 11/2003 |
| WO | WO 0062048 A2 | 10/2000 |

OTHER PUBLICATIONS

R. Thewes et al.: "Sensor Arrays for Fully Electronic DNA Detection on CMOS", ISSCC, Digist of Tech. Papers, 2002, pp. 350-351.

R. Hintsche et al.: Microelectrode arrays and application to biosensing devices >>, Biosensors & Bioelectronics, vol. 9, 1994, pp. 697-705.

R. Hintsche et al.: "Microbiosensors Using Electrodes Made in Si-Technology", Frontiers in Biosensorics, Fundamental Aspects, Dirk Hauser Verlag, Basel, 1997, pp. 267-283.

* cited by examiner

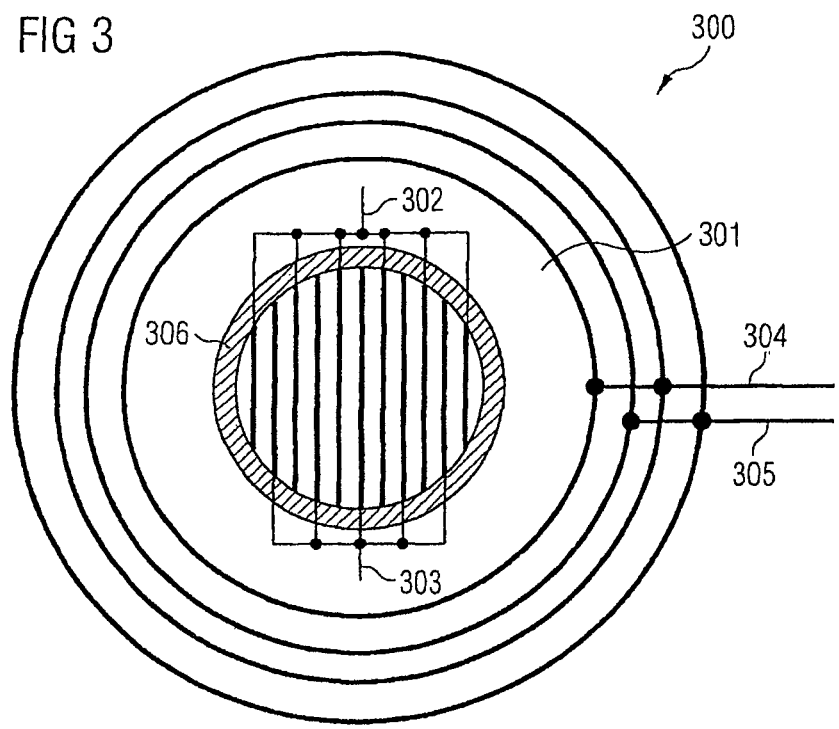
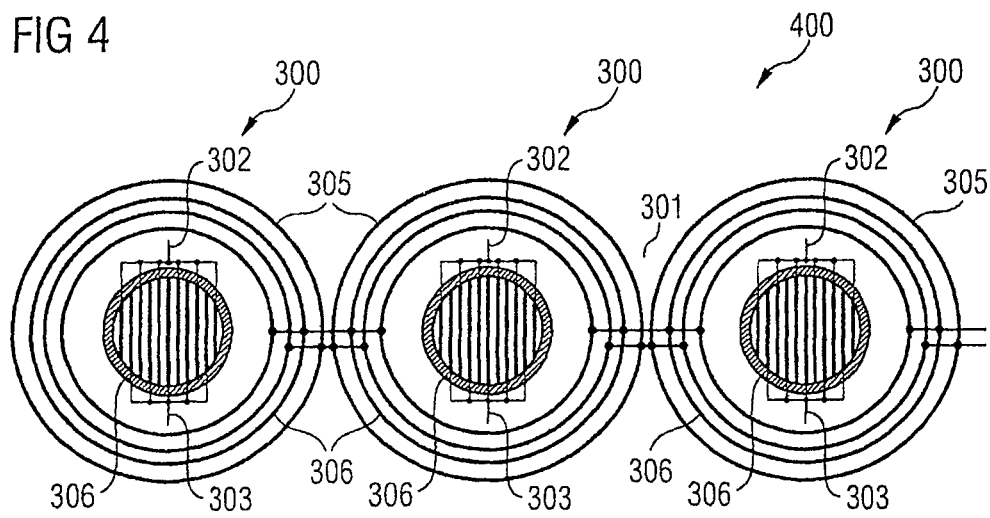

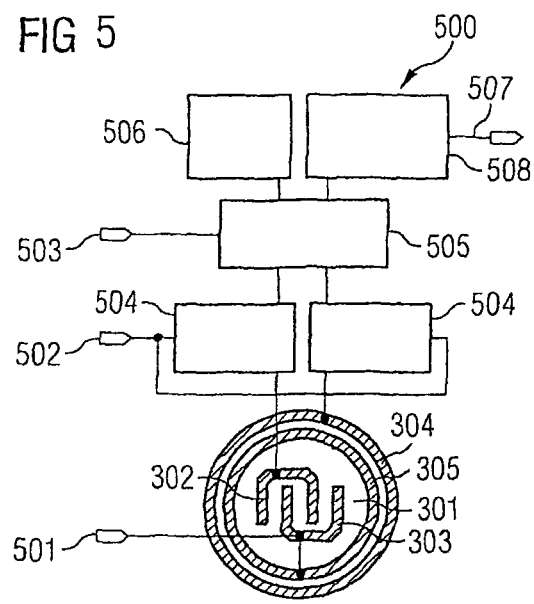
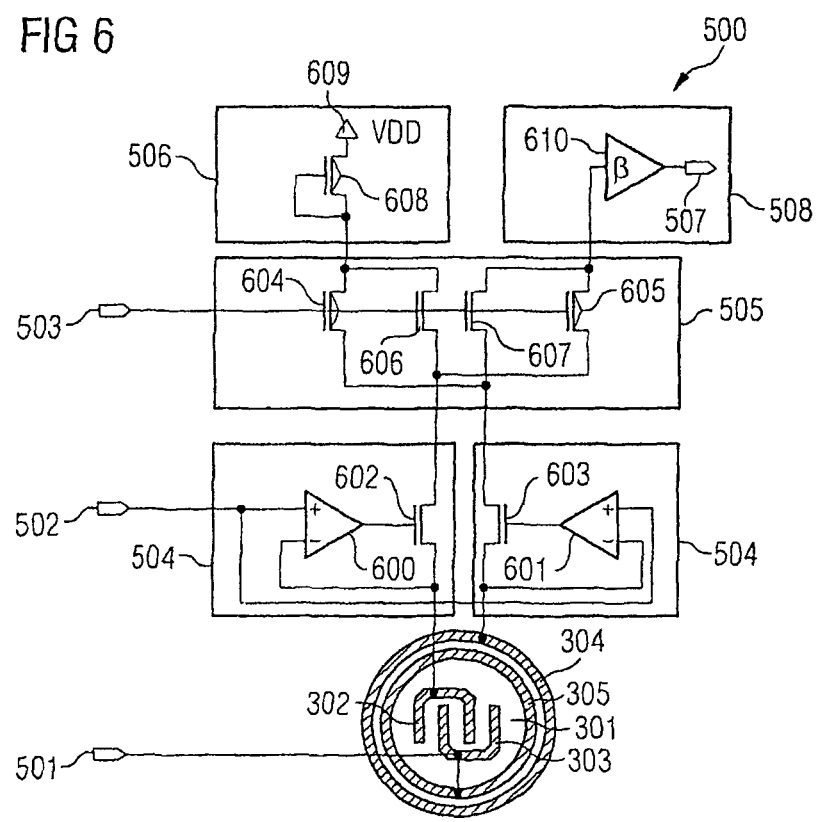

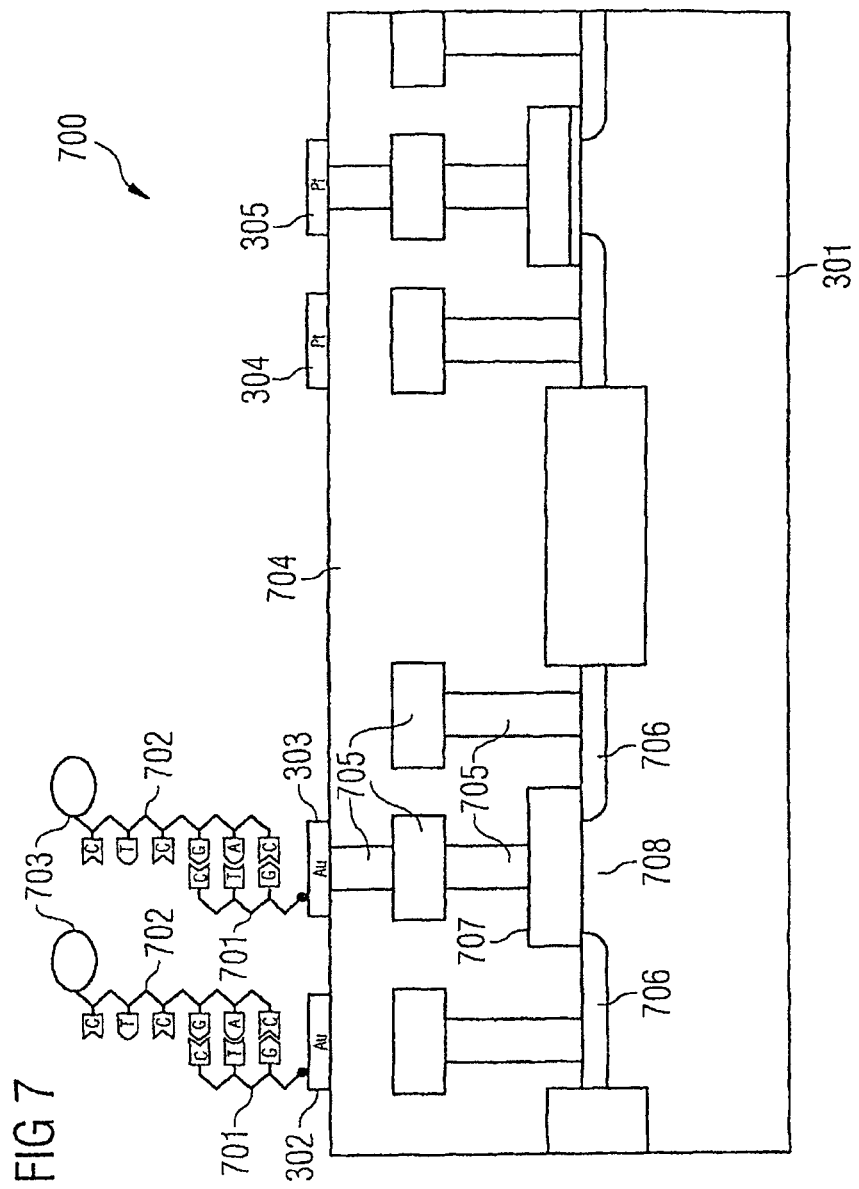

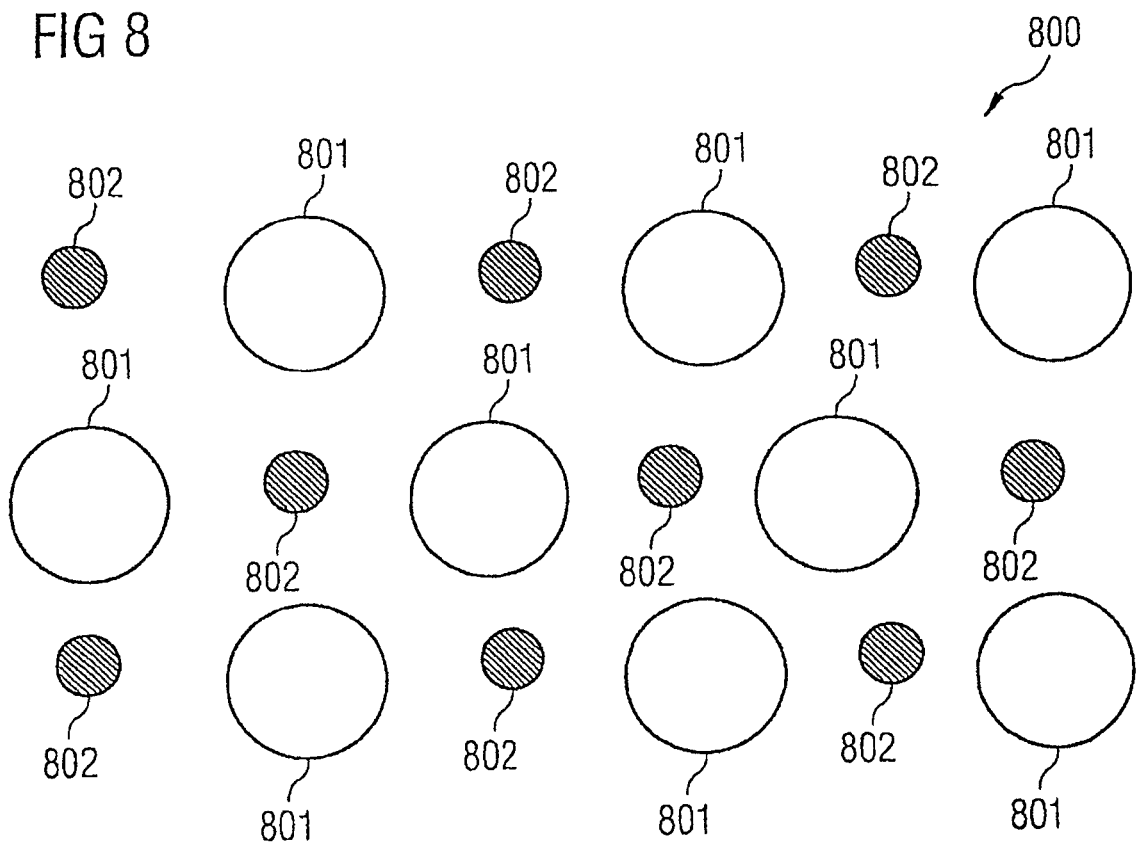

SENSOR ARRANGEMENT COMPRISING AN ELECTRODE FOR DETECTING DIFFUSED LOADED PARTICLES

PRIORITY STATEMENT

This application is the national phase under 35 U.S.C. § 371 of PCT International Application No. PCT/DE2005/000945 which has an International filing date of May 24, 2005, which designated the United States of America and which claims priority on German Patent Application number 10 2004 025 580.6 filed May 25, 2004, the entire contents of which are hereby incorporated herein by reference.

FIELD

The invention generally relates to a sensor arrangement, a sensor array and/or a method for producing a sensor arrangement.

BACKGROUND

Biosensors for detecting macromolecular biomolecules are increasingly gaining in importance. [1], [2] and [5] to [12] describe DNA sensors known from the prior art.

An important sensor type, particularly in the case of fully electronic DNA sensor chips, is so called redox cycling. The basics of redox cycling are described in [3], [4]. In redox cycling, macromolecular biopolymers are identified electronically on surfaces by detecting electric currents caused by means of redoxactive markings.

FIG. 1A, FIG. 1B show a redox cycling sensor arrangement 100 in accordance with the prior art.

The redox cycling sensor arrangement 100 has two gold working electrodes 101, 102 that are formed on a substrate 103. DNA capture molecules 104 having a prescribed sequence are immobilized on each working electrode 101, 102. The immobilization is performed, for example, in accordance with the so called gold-sulfur coupling. Furthermore, an analyte 105 to be examined is introduced into the redox cycling sensor arrangement 100. The analyte 105 can be, for example, an electrolytic solution with different DNA molecules.

If the analyte 105 contains first DNA half strands 106 with a sequence that is not complementary to the sequence of the DNA capture molecules 104, these first DNA half strands 106 do not hybridize with the DNA capture molecules 104 (see FIG. 1A). It is said there is a "mismatch" in this case.

If, by contrast, the analyte 105 contains second DNA half strands 107 with a sequence that is complementary to the sequence of the DNA capture molecules 104, these second DNA half strands 107 hybridize with the DNA capture molecules 104. It is said there is a "match" in this case. Otherwise expressed, a DNA half strand 104 of a prescribed sequence is respectively only capable of hybridizing selectively with a very specific DNA half strand, specifically with the DNA half strand with the sequence that is complementary to the respective capture molecule.

As FIG. 1B shows, the second DNA half strands 107 to be detected include a redoxactive marking 108. After the hybridization of the second DNA half strands 107 to be detected and having the DNA capture molecules 104, in the presence of suitable additional molecules 109 (for example para-aminophenylphosphate, p-APP) the redoxactive marking 108 (for example an enzyme label such as an alkaline phosphatase, for example) is used to initiate a cycle of oxidations and reductions of constituents of the additional molecules 109 that leads, to the accompaniment of interaction with the gold electrodes 101, 102, to the formation of reduced molecules 110 (for example para-aminophenol) or oxidized molecules 111 (for example quinoneimine). The cycle of oxidations and reductions leads to an electric ring current that enables the second DNA half strands 107 to be identified.

Consequently, in the case of a binding event between a particle to be detected and a capture molecule, a redoxactive species is generated in the redox cycling method by means of an enzyme label (for example an alkaline phosphatase), for example by converting para-aminophenylphosphate (p-APP) contained in an electrolyte into para-aminophenol. Since new redoxactive species are continuously generated, this leads to a rise in the electric current between the two electrodes.

An oxidizing electrical potential is required at the first working electrode 101, which is also denoted as generator electrode. A reducing electrical potential is required at the second working electrode 102, which is also denoted as collector electrode.

FIG. 2 shows an interdigital electrode arrangement 200 that is known from the prior art and has two working electrodes interlocking in the form of fingers, specifically a generator electrode 201 and a collector electrode 202. A reference electrode 203 and a counter electrode 204 are also shown. The electrodes 201 to 204 are formed on a substrate 205. An electrolytic analyte (not shown) that is coupled to the electrodes 201 to 204 can be applied to the interdigital electrode arrangement 200. The reference electrode 203 provides the electrical potential of the electrolytic analyte to an inverting input of a comparator 206 that compares it with the desired electrical potential at the noninverting input of the comparator 206.

In the event of a deviation of the electrical potential of the reference electrode 203 from the desired potential, the counter electrode 204 is driven via an output of the comparator 206 so that, if needed, it resupplies electric charge carriers in order to maintain the desired electrical potential of the electrolyte. Evidently, the reference electrode 203 forms a potentiostat device together with the comparator 206. The electrical potentials at the working electrodes 201, 202 are set relative to the reference voltage. Electric sensor currents of the generator electrode 201 or the collector electrode 202 are detected by means of first and second ammeters 207, 208 which contain information relating to a sensor event that may have occurred.

Also known from the prior art is a sensor array in the case of which a plurality of interdigital electrode arrangements 200 are interconnected, for example in the form of a matrix. Components 203, 204, 207, 208 for a number of sensor fields can be jointly provided therein.

If a sensor event occurs at a sensor field of such a sensor array, reduced molecules 110 or oxidized molecules 111 are formed. It is desired for these charged particles to be electrically detected at the working electrodes 201 and 202. However, these charged particles are frequently exposed to diffusion in an analyte and can undesirably diffuse to an adjacent sensor field (or an adjacent pixel) where they generate an undesired electric interference signal that falsifies the measurement event or generates a sensor signal at false sensor electrodes without a sensor event having taken place at these sensor electrodes.

An attempt is made in accordance with the prior art to meet this problem by selecting the measuring time to be so short that no undesired diffusion comes to bear, or remains negligibly small. This procedure is, however, disadvantageous, since it is then impossible to utilize the entire dynamics of the redox process for measuring. Otherwise expressed, given a measuring time selected to be too short, many electrically charged particles that are a consequence of a sensor event are lost in the measurement. Consequently, the sensitivity of identification is reduced or the signal-to-noise ratio is worsened.

In accordance with the prior art, [5] describes a method for detecting molecules or molecule complexes with the aid of an arrangement that has ultramicroelectrode arrays whose electrode structures are arranged so closely next to one another that the distances between the various structures lie in the ultramicro range. Use is made, in particular, of the effect that adjusting electric fields can be generated between closely adjacent electrodes, and the resulting current is influenced chiefly by the detected molecules and molecule complexes in the space near the electrodes. This influencing effect can be formed by diffusion, by accumulation or binding of the species to be measured.

[6] describes an electrical sensor array that has a number of sensor positions that respectively include at least two microelectrodes. This array can be used for simultaneously detecting various molecular substances from mixtures of substances in an electrochemical fashion. In particular, it is possible to address individual sensor positions individually.

[7] shows interdigital electrode arrangements on flexible substrates for the purpose of measuring the electrical behavior of substances. The arrangements contain electrode structures with a working electrode and a counter electrode.

[8] describes a biosensor array and a method for operating a biosensor array. The biosensor array has at least one first and one second signal line that are coupled to at least two of the biosensor fields. This provides a plurality of biosensor fields with joint signal lines for driving and detecting.

[9] describes a sensor for the qualitative and quantitative determination of (bio)organic oligomers and polymers. It is provided here at least one detection electrode on which capture molecules are immobilized for hybridization with organic oligomers and polymers that are to be determined, as well as at least two attraction electrodes on which no capture molecules are located. The detection electrode is arranged between the attraction electrodes in such a way that an analyte which possibly contains the chemical compounds to be detected and is applied to the sensor arrangement is moved away over the detection electrode by changing electric fields at the attraction electrodes, as a function of the type and size of the electric fields.

[10] shows a biosensor chip that has a first and a second electrode. The first electrode has a holding region for holding probe molecules that can bind macromolecular biopolymers. Also provided is an integrated electric differentiator circuit with which an electric current generated during a reduction/oxidation recycling operation is detected and can be differentiated with respect to time.

[11] describes an arrangement for an electrochemical analysis method and use thereof. This arrangement has an electrode system composed of at least three electrodes, at least one working electrode, one counter electrode and one reference electrode being present. The reference electrode is arranged in such a way that it is adjacent to at least subregions of the two further electrodes. It is preferably spaced apart equally from these subregions.

[12] describes a micro-multielectrode arrangement for the electrochemical measurement and generation of electroactive species, the electrodes being arranged on a carrier, in this case. One inner electrode and at least two further electrodes are provided, the inner electrode being connected as a reference electrode, and the further electrodes at least partially surrounding the inner electrode in the projection onto the carrier. The at least two further electrodes are a measuring electrode and a counter electrode, the counter electrode being arranged at a greater central distance from the reference electrode than the measuring electrode.

SUMMARY

At least one embodiment of the invention provides a sensor arrangement for detecting a particle possibly contained in an analyte, in which arrangement undesired effects based on a diffusion of electrically charged particles are effectively suppressed.

The sensor arrangement according to at least one embodiment of the invention for detecting particles possibly contained in an analyte contains a substrate and at least one sensor electrode arranged on and/or in the substrate and on which it is possible to immobilize capture molecules that are set up in such a way that they hybridize with particles to be detected that are possibly contained in an analyte, it being possible to detect electrically charged particles generated in a hybridization event at the at least one sensor electrode. Furthermore, the sensor arrangement of at least one embodiment of the invention contains at least one diffusion detection electrode that is arranged in a surrounding region of the at least one sensor electrode and is set up in such a way that it detects electrically charged particles that are diffusing away from the at least one sensor electrode and are generated in the event of a hybridization event.

Moreover, according to at least one embodiment of the invention, a sensor array is provided with a plurality of sensor arrangements that are formed on and/or in the substrate and has the above described features.

In the case of the method according to at least one embodiment of the invention for producing a sensor arrangement for detecting particles possibly contained in an analyte, at least one sensor electrode is formed on and/or in a substrate, capture molecules being immobilized on the at least one sensor electrode and being set up in such a way that they hybridize with particles to be detected that are possibly contained in an analyte, it being possible to detect electrically charged particles generated in a hybridization event at the at least one sensor electrode. Moreover, at least one diffusion detection electrode is formed in a surrounding region of the at least one sensor electrode and is set up in such a way that it detects electrically charged particles that are diffusing away from the at least one sensor electrode and are generated in the event of a hybridization event.

A basic idea of the invention is to be seen in making provision around one or more sensor electrodes or, otherwise, in a surrounding region of the sensor electrode(s) of an additional diffusion detection electrode that detects electrically charged particles (such as, for example, accumulate when there is a sensor event in the case of a redox cycling sensor) when these particles are diffusing away in an undesired fashion from the at least one sensor electrode. The diffusing away of particles from the surroundings of the sensor electrode can be used, for example as a trigger for ending a measurement so as to prevent the occurrence at adjacent sensor electrodes of artifacts that are to be ascribed to the particles which are diffusing away. It is thereby possible to determine exactly how long the measuring time is to be selected without falsifying, or otherwise negatively influencing, the measurement owing to electrically charged particles diffusing out of a sensor or region. Consequently, the dynamics of the redox process can, in turn, be utilized to the maximum such that the identification sensitivity of the sensor arrangement is significantly raised by comparison with the prior art.

The diffusion detection electrode can be fitted around the sensor electrode, for example, such that an annular, preferably continuous delimiting structure is provided with the aid of which a diffusion current can be reliably detected in all diffusion directions. The at least one diffusion detection electrode can also be provided from a number of subcomponents that are arranged, for example, in different directions in the surroundings of the at least one sensor electrode. For example, diffusion detection electrodes can form the structure similar to, or exactly in the same way as sensor electrodes, and/or be interconnected and be operated (for example by means of applying suitable electrical potentials) such that they fulfill the functionality of a diffusion detection electrode (specifically the detection of diffusion).

Otherwise expressed, the aim of at least one embodiment of the invention can be seen as fitting at least one additional diffusion detection electrode around a measuring pixel, or in a surrounding region thereof in any other way desired. Such a diffusion detection electrode can be designed, for example, as an additional interdigital structure that can exhibit one or more conductor tracks and otherwise can have a similar design, or can be connected up in a way similar to the at least one sensor electrode in the measuring pixel. By contrast with the measuring pixel (that is to say the at least one sensor electrode), the at least one diffusion detection electrode can be provided from another electrode material which can, for example, be set up in such a way that DNA strands cannot be immobilized there. However, it is also possible to use the same electrode material for the at least one sensor electrode and for the at least one diffusion detection electrode and, for example, to remove DNA strands immobilized in an undesired fashion on the at least one diffusion detection electrode from the at least one diffusion detection electrode for example by suitable voltage pulses (for example to burn them off).

As an example, platinum can be used as electrode material for the at least one diffusion detection electrode, since platinum prevents capture molecules from undesirably being immobilized on the diffusion detection electrode. The reason for this is that immobilizing DNA half strands as a typical example of capture molecules can be performed particularly effectively on gold because of the chemically particularly advantageous gold-thiol coupling (thiol: SH group), whereas immobilization does not take place on platinum or only in a negligible amount.

On the basis of a detection signal that is generated at the diffusion detection electrode, it is possible according to at least one embodiment of the invention to extend the duration of the measurement of the sensor event until a saturation signal is shown, or the diffusion detection electrode indicates a current that has been generated on the basis of the diffusion of redox particles. The measurement can then be stopped in order to prevent redox particles from undesirably falsifying the measuring signal.

Such a critical measurement occurs, for example, whenever a particularly strong hybridization event occurs at the sensor electrodes and a very high number of redox particles are therefore generated, and whenever there is no hybridization at the adjacent pixel or only a very weak one. The measurement of diffusion can then be used to show at which instant the diffusion of redox particles reaches the adjacent pixel, and can cause a falsification of the measuring signal there. The actual measurement of the sensor signal can then be ended in order to ensure a high reliability of the measurement.

Another advantage of the sensor arrangement according to at least one embodiment of the invention is to be seen in that the electric current (or in general, the electric detection signal), which does not originate from the redox current in the measuring pixel, can be measured and, if appropriate, subtracted from the measuring current. This undesired current can be generated by contaminants in the liquid or by p-APP undesirably entrained, and thereby falsify the measuring signal.

According to at least one embodiment, two sensor electrodes are provided that form an interdigital electrode arrangement. Otherwise expressed, the at least one sensor electrode can be implemented in a form similar to the working electrodes 201, 202 shown in FIG. 2.

The sensor arrangement can be set up as a biosensor arrangement.

In at least one embodiment, the sensor arrangement can be set up as a redox cycling arrangement that can be operated in accordance with the principle described with reference to FIG. 1A, FIG. 1B.

The sensor arrangement can be monolithically integrated in the substrate. The substrate can be a silicon substrate, in particular a silicon wafer or a silicon chip.

Furthermore, the sensor arrangement can have a compartmentalization device that is arranged around the at least one sensor electrode. Such a compartmentalization device, for example an annular structure, can be provided for the targeted application of a liquid drop to a sensor field.

It is possible to provide two diffusion detection electrodes that can be formed in an interlocking fashion. For example, the two diffusion detection electrodes can be substantially circular electrodes that are preferably concentric and have slightly different diameters. Again, each of the diffusion detection electrodes can be implemented by a number of rings that are toothed with the several rings of the other diffusion detection electrode.

The at least one diffusion detection electrode can surround the at least one sensor electrode in a substantially annular fashion. In particular, the diffusion detection electrode can have a circular or rectangular, triangular or otherwise polygonal structure, in particular also a honeycomb structure, that is easy to produce and can detect a diffusion in all directions.

The at least one diffusion detection electrode is preferably free of capture molecules. This can be ensured, for example, by producing the diffusion detection electrode from a material such as platinum on which capture molecules cannot be immobilized, or can be only poorly immobilized.

The sensor arrangement can have a control device that is coupled to the at least one diffusion detection electrode and is set up in such a way that it ends a detection operating state when a signal at the at least one diffusion detection electrode reaches a prescribed threshold value or exceeds it. Denoted here as detection operating states is an operating state of the sensor arrangement in the case of which a sensor event in the form of a sensor current, a sensor voltage etc. is detected at the at least one sensor electrode. If the diffusion of electrically charged particles from the region of the at least one sensor electrode reaches a prescribed threshold value, the diffusion also generates a signal at the at least one diffusion detection electrode. If this signal exceeds a threshold value, the control device uses this as a trigger for ending a detection operating state, since detection signals detected later in time are defective because of the undesired diffusing away of electrically charged particles.

Furthermore, the control device can be coupled to the at least one sensor electrode and be set up in such a way that it ends a detection operating state when a signal of the at least one sensor electrode reaches a saturation state. In accordance with this development, it is taken into account that even without an undesired diffusion of electrically charged particles from a surrounding region of the at least one sensor electrode, a measurement should be terminated whenever a measuring signal at the at least one sensor electrode has already gone into saturation. This scenario is also taken into account by the described set up of the control device.

In particular, the sensor arrangement can have a first and a second sensor electrode, a first and a second diffusion detection electrode and a potential control device that is set up in such a way that it provides the first sensor electrode and the first diffusion detection electrode with an electrical reference potential, and is set up for controlling the electrical potential of the second sensor electrode and of the second diffusion detection electrode.

Furthermore, a signal processing device can be provided for processing a signal of the second sensor electrode and/or of the second diffusion detection electrode.

Moreover, it is possible to provide a multiplex device that selectively couples the signal processing device with the second sensor electrode or with the second diffusion detection electrode.

Although the described refinements have been described with reference to the sensor arrangement according to at least one embodiment of the invention, they also are valid for the sensor array having a plurality of sensor arrangements.

Refinements of the sensor array are described below.

An amplifier device for amplifying a detected signal can be provided for the at least one sensor electrode and/or for the at least one diffusion detection electrode. Such an amplifier can be provided separately for each of the electrodes or, alternatively, by way of a common amplifier device jointly for a number or all of the sensor arrangements of a sensor array.

In the case of the sensor array, diffusion detection electrodes can be arranged in regions between sensor electrodes of different sensor arrangements. Each redox cycling sensor arrangement contains at least one sensor electrode and at least one diffusion detection electrode arranged in a surrounding region thereof. The diffusion detection electrodes can be formed between sensor electrodes of different sensor arrangements.

According to at least one embodiment of the invention, a diffusion detection electrode need not necessarily completely surround a sensor electrode, but it suffices that a sufficiently large surrounding region of a sensor electrode is surrounded by an adjacent or several adjacent diffusion detection electrodes such that in the case of the diffusing away of charge carriers at least one of the adjacent diffusion detection electrodes can detect a diffusion event. A diffusion detection electrode can therefore serve for detecting the diffusion of a number of sensor electrodes that border on a respective diffusion detection electrode.

Embodiments of the inventive method for producing a sensor arrangement is described in more detail below.

Refinements of embodiments of the sensor arrangement are also valid for the method for producing the sensor arrangement, and vice versa.

The at least one diffusion detection electrode is preferably kept free of capture molecules. This can be achieved by providing the at least one diffusion detection electrode from a material on which capture molecules cannot be immobilized, for example platinum. Gold is a material on which capture molecules can be immobilized particularly effectively. Consequently, a combination is particularly advantageous in the case of which the at least one diffusion detection electrode is produced from platinum, and in the case of which the at least one sensor electrode is produced from gold.

Alternatively, the at least one diffusion detection electrode can be kept free of capture molecules by firstly also immobilizing capture molecules on the at least one diffusion detection electrode, and subsequently selectively removing the capture molecules from the at least one diffusion detection electrode, whereas capture molecules remain on the at least one sensor electrode. This can be implemented in that the immobilized capture molecules (for example DNA half strands) are burned off only from the diffusion detection electrodes by applying suitable voltage pulses. Otherwise expressed, the capture molecules can be removed from the at least one diffusion detection electrode by means of applying an electrical potential to the at least one diffusion detection electrode.

BRIEF DESCRIPTION OF THE DRAWINGS

Example embodiments of the invention are illustrated in the figures and are explained in more detail further below.

In the drawings:

FIG. 3 shows a sensor arrangement in accordance with a first example embodiment of the invention, FIG. 4 shows a sensor array in accordance with a first example embodiment of the invention, FIG. 5 shows a sensor arrangement in accordance with a second example embodiment of the invention, FIG. 6 shows a detailed illustration of the sensor arrangement shown in FIG. 5, FIG. 7 shows a cross-sectional view of a sensor arrangement in accordance with a third example embodiment of the invention, and FIG. 8 shows a sensor array in accordance with a second example embodiment of the invention.

Identical or similar components in different figures are provided with identical reference symbols.

The illustrations in the figures are schematic and not to scale.

DETAILED DESCRIPTION OF THE EXAMPLE EMBODIMENTS

A sensor arrangement 300 in accordance with a first example embodiment of the invention is described below with reference to FIG. 3.

Figure 1A:
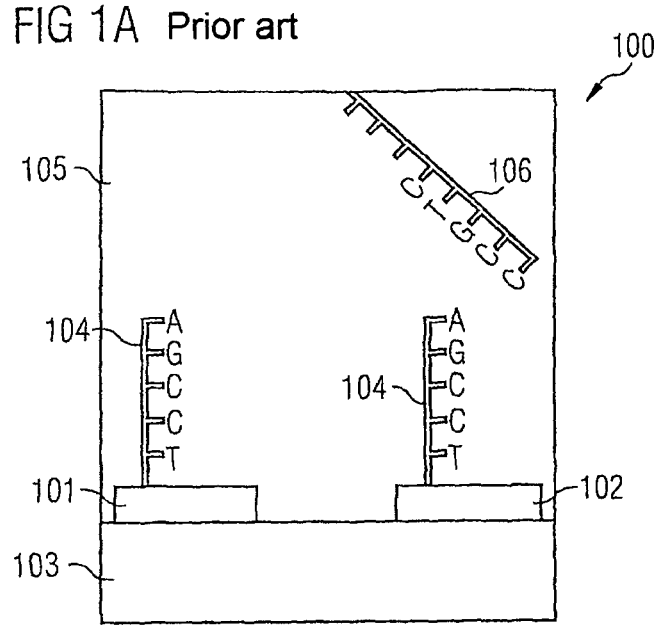
FIGS. 1A, 1B show different operating states of a redox cycling sensor arrangement in accordance with the prior art.
Figure 1B:
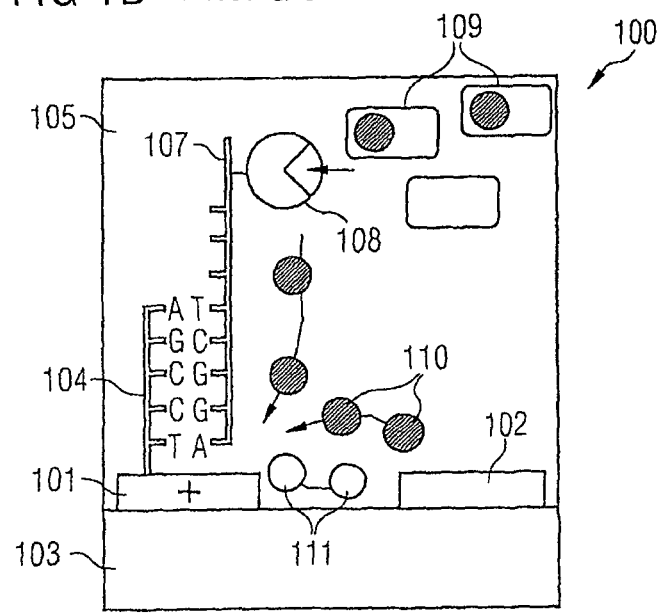
Figure 2:
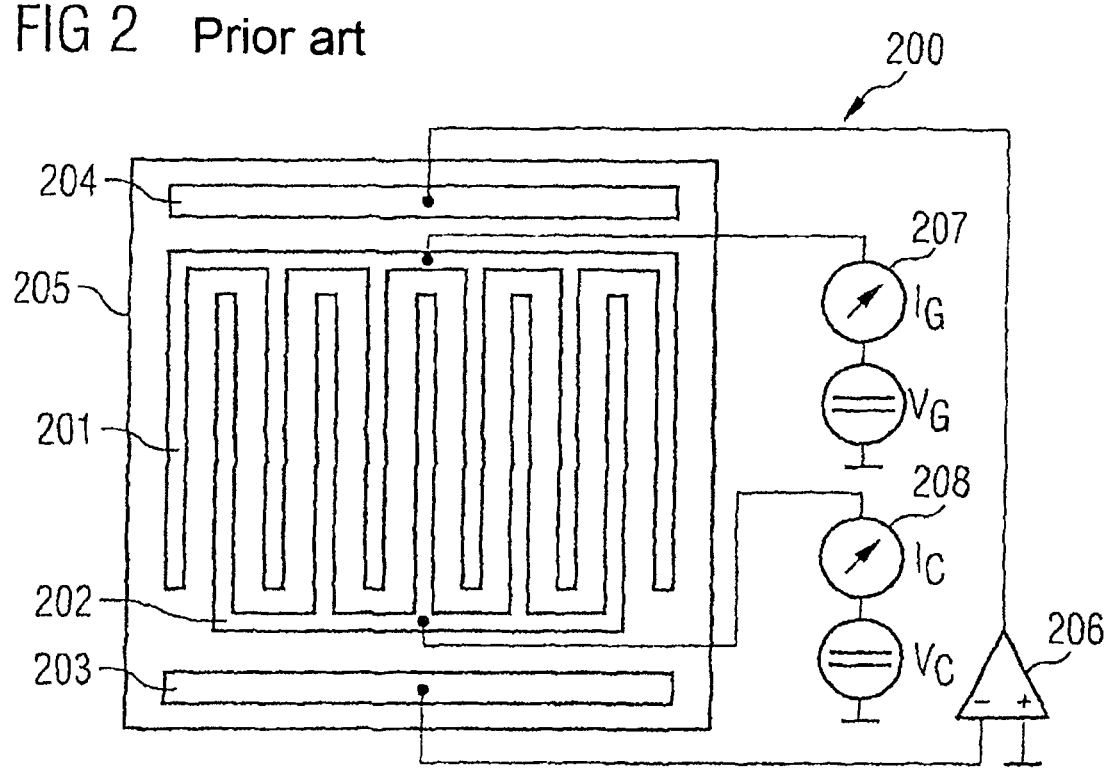
FIG. 2 shows an interdigital electrode arrangement in accordance with the prior art.

The sensor arrangement 300 for detecting particles possibly contained in an analyte is monolithically integrated in or on a silicon substrate 301. The sensor arrangement 300 includes a first sensor electrode 302 and a second sensor electrode 303 that are provided as an interdigital electrode arrangement interlocking in the form of fingers. Immobilized on both sensor electrodes 302, 303 as capture molecules are DNA half strands (not shown) which are set up in such a way that they can hybridize with particles to be detected that are possibly contained in an analyte, it being possible for electrically charged particles generated in the case of a hybridization event to be detected as an electric sensor current at the sensor electrodes 302, 303, in accordance with the principle described with reference to FIG. 1A, FIG. 1B, or the redox cycling sensor.

Furthermore, as shown in FIG. 3, there are formed in a surrounding region of the sensor electrodes 302, 303 a first diffusion detection electrode 304 and a second diffusion detection electrode 305 which are set up in such a way that they detect electrically charged particles diffusing away from the sensor electrodes 302, 303 and generated in a hybridization event. The diffusion detection electrodes 304, 305 are respectively implemented as a plurality of concentric rings, two diffusion detection electrodes 304, 305 being provided in an interlocking fashion. Furthermore, a compartmentalization ring 306 is formed around the sensor electrodes 302, 303. The diffusion detection electrodes 304, 305 made from platinum material are free of capture molecules. The capture molecules are immobilized on the sensor electrodes 302, 303 made from gold material, this being done by using the gold-sulfur bond.

In the case of a sensor event between DNA half strands as capture molecules on the sensor electrodes 302, 303 and complementary DNA half strands, that are to be detected, in an analyte, which complementary DNA half strands have a redoxactive label, there are generated near the sensor electrodes 302, 303, in accordance with the principle of redox cycling, electrically charged redox particles that effect an electric sensor current at the sensor electrodes 302, 303.

These electrically charged particles are exposed to the influence of the diffusion in an analyte, and can diffuse out of the region of the sensor electrodes 302, 303. If such electrically charged particles leave the surrounding region of the sensor electrodes 302, 303, and if they reach the diffusion detection electrodes 304, 305, they then generate at the diffusion detection electrodes 304, 305 a sensor signal that can be detected and contains information that a measurement at later points in time is therefore problematic because electrically charged sensor particles are leaving the redox cycling sensor arrangement 300 or have already done so. This can be used as the trigger signal for the ending of a measurement.

A sensor array 400 in accordance with a first example embodiment of the invention is described in what follows with reference to FIG. 4.

The redox cycling sensor array 400 includes a plurality of redox cycling sensor arrangements 300. Here, the electrical connections of the first diffusion detection electrodes 304 of the several redox cycling sensor arrangements 300 are coupled to one another, and the second diffusion detection electrodes 305 of the several redox cycling sensor arrangements 300 are coupled to one another. The number of required connections of the arrangement is thereby reduced.

A redox cycling sensor arrangement 500 in accordance with a second example embodiment of the invention is described in what follows with reference to FIG. 5.

Once again, a first sensor electrode 302 and a second sensor electrode 303 are shown that are provided in interlocking fashion in the form of fingers and on which capture molecules (not shown) are immobilized. A first diffusion detection electrode 304 and a second diffusion detection electrode 305 are provided in a surrounding region of the sensor electrodes 302, 303 and surrounding them in an annular fashion. The second sensor electrode 303 and the second diffusion detection electrode 305 are brought to a first electrical potential 501.

A second electrical potential 502 is provided for a potential control device 504 that is connected to the first sensor electrode 302 and to the first diffusion detection electrode 304. The potential control device 504 is coupled to a selection circuit 505 that is provided with a third electrical potential 503. The selection circuit 505 is coupled both to an auxiliary current source 506 and to a signal processing circuit 508 for processing provided output signals, it being possible for the signal processing circuit 508 to provide a preprocessed output signal at a signal output 507.

The inventive sensor structure is thus illustrated in FIG. 5 with an efficient circuitry. The second sensor electrode 303 and the second diffusion detection electrode 305 are directly supplied with an electric voltage of the first electrical potential 501. The first sensor electrode 302 and the first diffusion detection electrode 304 are operated by using the potential control device 504 such that the generated current signal is available for further processing and evaluation. In order to keep the space required for the circuit low, the signal processing circuit 508 is provided jointly and not for the sensor electrodes 302, 303 on the one hand and for the diffusion detection electrodes 304, 305 on the other. Consequently, the current processing circuit 508 is multiplexed with the aid of the selection circuit 505. The electrode respectively not selected from the group of the first sensor electrode 302 and the first diffusion detection electrode 304 can respectively be coupled to the auxiliary current source 506.

FIG. 6 shows once again the redox cycling sensor arrangement 500, an example implementation in terms of circuitry being illustrated for the individual components 504 to 508.

The potential control device 504 has a first comparator 600 whose non-inverting input is brought to the second electrical potential 502 and is coupled to the inverting input of a second comparator 601. Furthermore, one output of the first comparator 600 is coupled to a gate terminal of a first n-MOS field effect transistor 602 whose first source/drain terminal is coupled to the inverting input of the first comparator 600 and to the first sensor electrode 302. Furthermore, the inverting input of the second comparator 601 is coupled to the first diffusion detection electrode 304 and to a first source/drain terminal of a second n-MOS field effect transistor 603, whose gate terminal is coupled to an output of the second comparator 601.

The second source/drain terminal of the second n-MOS field effect transistor 603 is coupled to a first source/drain terminal of a first p-MOS field effect transistor 604 and to a first source/drain terminal of a fourth n-MOS field effect transistor 607. Furthermore, a second source/drain terminal of the first n-MOS field effect transistor 602 is coupled to a first source/drain terminal of a third n-MOS field effect transistor 606 and of a second p-MOS field effect transistor 605. The gate terminal of the transistors 604 to 607, which transistors 604 to 607 form the selection circuit 505, are brought to the third electrical potential 503.

The second source/drain terminals of the first p-MOS field effect transistor 604 and of the third n-MOS field effect transistor 606 are coupled to a first source/drain terminal and to the gate terminal of a third p-MOS field effect transistor 608 of the auxiliary current source 606. The second source/drain terminal of the third p-MOS field effect transistor 608 is brought to the supply potential VDD 609. Furthermore, the second source/drain terminals of the second p-MOS field effect transistor 605 and of the fourth n-MOS field effect transistor 607 are coupled to an input of an amplifier 610 whose output is coupled to the signal output 507. The amplifier 610 is part of the signal processing circuit 508.

The example embodiment, shown in FIG. 6, of the electronic configuration shows that the potential control device 504 is implemented with the aid of OTAs 600, 601 (Operational Transconductance Amplifiers) and by current control transistors 602, 603. Selection circuit 505 is formed from two n-MOS switching transistors 606, 607 and from two p-MOS switching transistors 604, 605. The auxiliary current source 506 is designed as a p-MOS diode 608. In FIG. 6, the current signal processing circuit 508 is a current amplifier circuit, and so the output signal at the signal output 507 is an analog signal. It is also possible to operate an ADC circuit (Analog-to-Digital Converter), and thus to obtain a digital output signal.

A redox cycling sensor arrangement 700 in accordance with a third example embodiment of the invention is described in what follows with reference to FIG. 7.

FIG. 7 shows a cross-sectional view of a monolithically integrated sensor arrangement 700. The redox cycling sensor arrangement 700 is monolithically integrated in a silicon substrate 301. First and second sensor electrodes 302, 303 made from gold material are formed on the surface of the redox cycling sensor arrangement 700. DNA half strands 701 are immobilized as capture molecules on the sensor electrodes 302, 303 by using the gold-sulfur bond. First and second diffusion detection electrodes 304, 305 made from platinum material are formed on other surface regions of the redox cycling sensor arrangement 700. Platinum material has the property that capture molecules 701 cannot be immobilized thereon, and so the diffusion detection electrodes 304, 305 are free of capture molecules 701. FIG. 7 shows the redox cycling sensor arrangement 700 in an operating state in which particles 702 that are to be detected and on which redoxactive labels 703 are fitted have been hybridized with capture molecules 701. In accordance with the principle described with reference to FIG. 1A, FIG. 1B, electrically charged particles are generated that can be identified at the sensor electrodes 302, 303. If such electrically charged particles leave the surrounding region of the sensor electrodes 302, 303, and if they reach the diffusion detection electrodes 304, 305 arranged outside the sensor electrodes 302, 303, an appropriate signal can be generated at the diffusion detection electrodes 304, 305.

As is further shown in FIG. 7, there is provided between the silicon substrate 301 and the electrodes 302 to 305 a CMOS circuit that is formed from electrically charged contact-making elements 705 in a silicon oxide layer 704, and from additional components (not shown in FIG. 7). The contact-making elements 705 make an electrical coupling between the sensor electrodes 302 to 305, on the one hand, and electronic evaluation components formed deeper in the redox cycling sensor arrangement 700, on the other hand. For example, via electrically conductive contact-making elements the second sensor electrode 303 is coupled to the gate region 705 of a readout transistor whose source/drain regions 706 are provided in the silicon substrate 301 as doped regions, a region 708 between the source/drain regions 706 and below the gate region 707 serving as channel region. On-chip sensor signals of the sensor electrodes 302, 303 and diffusion signals of the diffusion detection electrodes 304, 305 can be evaluated in this way and be used for controlling and/or for forming a sensor signal of the redox cycling sensor arrangement 700.

It is to be noted that in FIG. 7 only a portion of the components of the redox cycling sensor arrangement 700 is shown, in particular the diffusion detection electrodes 304, 305 are arranged in annular fashion around the sensor electrodes 302, 303 interlocking in the form of fingers, in order to completely enclose a surrounding region of the sensor electrodes 302, 303.

A sensor array 800 in accordance with a second example embodiment of the invention is described in what follows with reference to FIG. 8.

The redox cycling sensor array 800 includes a plurality of redox cycling sensor arrangements. Each redox cycling sensor arrangement includes a sensor electrode 801 and diffusion detection electrodes 802 that are arranged in a surrounding region thereof. In accordance with FIG. 8, the diffusion detection electrodes 802 are formed between the sensor electrodes 801 arranged in the form of a matrix. Consequently, according to the invention a diffusion detection electrode 802 need not necessarily completely surround a sensor electrode 801; instead, it is sufficient for a sufficiently large surrounding region of a sensor electrode 801 to be surrounded by adjacent diffusion detection electrodes 802 such that in the case of the diffusing away of charge carriers at least one of the adjacent diffusion detection electrodes 802 detects the diffusion event. Thus, in accordance with FIG. 8 a diffusion detection electrode 802 serves for detecting the diffusion of a number of sensor electrodes 801, specifically, in particular, of all those sensor electrodes 801 that border on a respective diffusion detection electrode 802.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The following publications are cited in this document:

[1] Hofmann, F et al. "Passive DNA Sensor with Gold Electrodes Fabricated in a CMOS Backend Process" Proc. ESSDERC 2002, Digist of Tech. Papers, pages 487 to 490
[2] Thewes, R et al. "Sensor Arrays for Fully Electronic DNA Detection on CMOS", ISSCC, Digist of Tech. Papers, 2002, pages 350 to 351
[3] Hintsche, R et al. "Microelectrode arrays and application to biosensing devices", Biosensors & Bioelectronics, Vol. 9, pages 697 to 705, 1994
[4] Hintsche, R et al. "Microbiosensors Using Electrodes Made in Si-Technology", Frontiers in Biosensorics, Fundamental Aspects, F. W. Scheller et al. (eds.), Dirk Hauser Verlag, Basel, pages 267 to 283, 1997
[5] DE 196 10 115 A1
[6] WO 00/62048
[7] US 2003/0155237 A1
[8] DE 192 28 124 A1
[9] DE 102 14 719 A1
[10] DE 100 15 816 A1
[11] DE 100 58 397 A1
[12] DD 301 930 A9

LIST OF REFERENCE NUMERALS

100 Redox cycling sensor arrangement
101 First gold working electrode
102 Second gold working electrode
103 Substrate
104 DNA capture molecules
105 Analyte
106 First DNA half strands
107 Second DNA half strands
108 Redoxactive marking
109 Additional molecules
110 Reduced molecules
111 Oxidized molecules
200 Interdigital electrode arrangement
201 Generator electrode
202 Collector electrode
203 Reference electrode
204 Counter electrode
205 Substrate
206 Comparator
207 First ammeter
208 Second ammeter
300 Redox cycling sensor arrangement
301 Silicon substrate
302 First sensor electrode
303 Second sensor electrode
304 First diffusion detection electrode 305 Second diffusion detection electrode
306 Compartmentalization ring
400 Redox cycling sensor array
500 Redox cycling sensor arrangement
501 First electrical potential
502 Second electrical potential
503 Third electrical potential
504 Potential control device
505 Selection circuit
506 Auxiliary current source
507 Signal output
508 Signal processing circuit
600 First comparator
601 Second comparator
602 First n-MOS field effect transistor
603 Second n-MOS field effect transistor
604 First p-MOS field effect transistor
605 Second p-MOS field effect transistor
606 Third n-MOS field effect transistor
607 Fourth n-MOS field effect transistor
608 Third p-MOS field effect transistor
609 Supply potential
610 Amplifier
700 Redox cycling sensor arrangement
701 DNA half strands
702 DNA half strands to be detected
703 Label molecules
704 Silicon oxide layer
705 Contact-making elements
706 Source/drain regions
707 Gate region
708 Channel region
800 Redox cycling sensor array
801 Sensor electrodes
802 Diffusion detection electrodes

The invention claimed is:

1. A sensor arrangement for detecting particles contained in an analyte, comprising:
 a substrate;
 at least one sensor electrode arranged at least one of on and in the substrate;
 capture molecules immobilizable on the at least one sensor electrode, the capture molecules being set up in such a way that the capture molecules hybridize with particles to be detected that are contained in an analyte, electrically charged particles generated in the hybridization event being detectable at the at least one sensor electrode;
 at least one diffusion detection electrode, arranged in a surrounding region of the at least one sensor electrode, set up in such a way that the at least one diffusion detection electrode detects electrically charged particles that are diffusing away from the at least one sensor electrode and are generated in the event of the hybridization event; and
 a control device, coupled to the at least one diffusion detection electrode, set up in such a way that the control device ends a detection operating state when a signal at the at least one diffusion detection electrode reaches a threshold value.

2. The sensor arrangement as claimed in claim 1, wherein the arrangement includes two sensor electrodes that form an interdigital electrode arrangement.

3. The sensor arrangement as claimed in claim 1, set up as a biosensor arrangement.

4. The sensor arrangement as claimed in claim 1, set up as a redox cycling arrangement.

5. The sensor arrangement as claimed in claim 1, monolithically integrated in the substrate.

6. The sensor arrangement as claimed in claim 1, further comprising a compartmentalization device, arranged around the at least one sensor electrode.

7. The sensor arrangement as claimed in claim 1, wherein the arrangement includes two diffusion detection electrodes, provided in an interlocking fashion.

8. The sensor arrangement as claimed in claim 1, wherein the at least one diffusion detection electrode surrounds the at least one sensor electrode in a substantially annular fashion.

9. The sensor arrangement as claimed in claim 1, wherein the at least one diffusion detection electrode is free of capture molecules.

10. The sensor arrangement as claimed in claim 1, wherein the control device is coupled to the at least one sensor electrode and is set up in such a way that it ends a detection operating state when a signal at the at least one sensor electrode reaches a saturation state.

11. The sensor arrangement as claimed in claim 1, wherein the arrangement includes a first and a second sensor electrode, a first and a second diffusion detection electrode and the control device is set up in such a way that it provides the first sensor electrode and the first diffusion detection electrode with an electrical reference potential, and is set up for controlling the electrical potentials of the second sensor electrode and of the second diffusion detection electrode.

12. The sensor arrangement as claimed in claim 11, further comprising a signal processing device for processing a signal of at least one of the second sensor electrode and the second diffusion detection electrode.

13. The sensor arrangement as claimed in claim 12, further comprising a multiplexer device that selectively couples the signal processing device with the second sensor electrode or with the second diffusion detection electrode.

14. A sensor array comprising a plurality of sensor arrangements, formed at least one of on and in the substrate, as claimed in claim 1.

15. The sensor array as claimed in claim 14, further comprising an amplifier device for amplifying a signal of the at least one diffusion detection device, the amplifier device being provided jointly for a plurality of the sensor arrangements.

16. The sensor array as claimed in claim 14, wherein diffusion detection electrodes are arranged in regions between sensor electrodes of different sensor arrangements.

17. A method for producing a sensor arrangement for detecting particles contained in an analyte, comprising:
 forming at least one sensor electrode at least one of on and in a substrate;
 immobilizing capture molecules on the at least one sensor electrode and setting them up in such a way that the capture molecules hybridize with particles to be detected that are contained in an analyte, electrically charged particles generated in the hybridization event being detectable at the at least one sensor electrode; and
 forming at least one diffusion detection electrode in a surrounding region of the at least one sensor electrode and setting the at least one diffusion detection electrode up in such a way that the at least one diffusion detection electrode detects electrically charged particles that are diffusing away from the at least one sensor electrode and are generated in the event of the hybridization event.

18. The method as claimed in claim 17, wherein the at least one diffusion detection electrode is kept free of capture molecules by providing the at least one diffusion detection electrode with a material on which capture molecules cannot be immobilized.

19. The method as claimed in claim 17, wherein the at least one diffusion detection electrode is kept free of capture molecules by firstly immobilizing capture molecules on the at least one diffusion detection electrode and subsequently removing the capture molecules from the at least one diffusion detection electrode.

20. The method as claimed in claim 19, wherein the capture molecules are removed from the at least one diffusion detection electrode by applying an electrical potential to the at least one diffusion detection electrode.

21. The sensor arrangement as claimed in claim 2, set up as a biosensor arrangement.

22. The sensor arrangement as claimed in claim 2, set up as a redox cycling arrangement.

23. The sensor arrangement as claimed in claim 2, monolithically integrated in the substrate.

24. The sensor array as claimed in claim 15, wherein the diffusion detection electrodes are arranged in regions between the sensor electrodes of different sensor arrangements.

* * * * *